(12) United States Patent
Hautvast et al.

(10) Patent No.: US 10,092,444 B2
(45) Date of Patent: Oct. 9, 2018

(54) SYSTEM FOR APPLYING RADIATION TO A TARGET REGION WITHIN A SUBJECT

(71) Applicant: KONINKLIJKE PHILIPS N.V., Eindhoven (NL)

(72) Inventors: Guillaume Leopold Theodorus Frederik Hautvast, Veldhoven (NL); Dirk Binnekamp, Borne (NL)

(73) Assignee: Koninklijke Philips N.V., Eindhoven (NL)

( * ) Notice: Subject to any disclaimer, the term of this patent is extended or adjusted under 35 U.S.C. 154(b) by 60 days.

(21) Appl. No.: 15/121,392

(22) PCT Filed: Feb. 26, 2015

(86) PCT No.: PCT/EP2015/053962
§ 371 (c)(1),
(2) Date: Aug. 25, 2016

(87) PCT Pub. No.: WO2015/128392
PCT Pub. Date: Sep. 3, 2015

(65) Prior Publication Data
US 2016/0361194 A1    Dec. 15, 2016

(30) Foreign Application Priority Data

Feb. 27, 2014  (EP) .................................... 14156948
Nov. 19, 2014  (EP) .................................... 14193853

(51) Int. Cl.
*A61N 5/00* (2006.01)
*A61F 7/00* (2006.01)
(Continued)

(52) U.S. Cl.
CPC ................ *A61F 7/00* (2013.01); *A61B 18/24* (2013.01); *A61N 1/406* (2013.01); *A61N 5/025* (2013.01);
(Continued)

(58) Field of Classification Search
CPC ............... A61N 5/00; A61N 5/01; A61N 5/10
(Continued)

(56) References Cited

U.S. PATENT DOCUMENTS 7,582,050 B2    9/2009   Schlorff et al.
7,717,618 B2    5/2010   Saxena et al.
(Continued)

FOREIGN PATENT DOCUMENTS

DE        3739749 A1      6/1989
KR    20100118177 A      11/2010
WO     2014064552 A1      5/2014

OTHER PUBLICATIONS

Yu, F.T.S. et al., "Fiber Optic Sensors", Marcel Dekker Inc., (2002), chapter 4.
(Continued)

*Primary Examiner* — John Lacyk

(57) ABSTRACT

The invention relates to a system for applying radiation to a target region within a subject. An introduction element (12) like a brachytherapy catheter is inserted into the subject and a radiation source (10) is moved within the introduction element such that it is located within or close to the target region. The target region is heated, wherein the movement of the radiation source within the introduction element is controlled depending on the temperature along the introduction element. The susceptibility of the subject for the radiation emitted by the radiation source at a respective location along the length of the introduction element can depend on the temperature at the respective location such that by controlling the movement of the radiation source depending on the temperature along the length of the introduction element the application of the radiation can be optimized.

15 Claims, 6 Drawing Sheets

(51) Int. Cl.

| | |
|---|---|
| *A61N 5/10* | (2006.01) |
| *A61B 18/24* | (2006.01) |
| *A61N 1/40* | (2006.01) |
| *A61N 5/02* | (2006.01) |
| *A61N 7/02* | (2006.01) |
| *A61B 18/14* | (2006.01) |
| *A61B 18/18* | (2006.01) |
| *A61B 18/00* | (2006.01) |
| *A61B 18/22* | (2006.01) |
| *A61B 34/20* | (2016.01) |
| *A61B 90/00* | (2016.01) |
| *A61B 17/34* | (2006.01) |
| *A61N 5/067* | (2006.01) |

(52) U.S. Cl.
CPC ......... *A61N 5/1001* (2013.01); *A61N 5/1027* (2013.01); *A61N 5/1039* (2013.01); *A61N 5/1071* (2013.01); *A61N 7/022* (2013.01); *A61B 18/14* (2013.01); *A61B 18/1815* (2013.01); *A61B 2017/3413* (2013.01); *A61B 2018/00642* (2013.01); *A61B 2018/00666* (2013.01); *A61B 2018/00791* (2013.01); *A61B 2018/00982* (2013.01); *A61B 2018/2294* (2013.01); *A61B 2034/2061* (2016.02); *A61B 2090/378* (2016.02); *A61F 2007/0086* (2013.01); *A61F 2007/0088* (2013.01); *A61F 2007/0096* (2013.01); *A61N 5/103* (2013.01); *A61N 5/1048* (2013.01); *A61N 7/02* (2013.01); *A61N 2005/067* (2013.01)

(58) Field of Classification Search
USPC ....................................................... 600/1–8
See application file for complete search history.

(56) References Cited

U.S. PATENT DOCUMENTS

| | | |
|---|---|---|
| 8,360,950 B2 | 1/2013 | Acosta et al. |
| 8,874,230 B2 | 10/2014 | Niver et al. |
| 2014/0058384 A1 | 2/2014 | Buysse et al. |
| 2016/0361194 A1 | 12/2016 | Hautvast et al. |

OTHER PUBLICATIONS

Khokhlova, T., et al., "HIFU for palliative treatment of pancreatic cancer", vol. 2, No. 3, pp. 175-184, Journal of Gastrointestinal Oncology (2011).

Stea, B., et al., "Interstitial thermoradiotherapy of brain tumors: Preliminary results of a phase I clinical trial", International Journal of Radiation: Oncology Biology Physics, vol. 19, No. 6, (1990), pp. 1463-1471.

Wang, Z., et al., "Elimination of dose-rate effects by mild hyperthermia", International Journal of Radiation: Oncology Biology Ph7sics, vol. 24, No. 5, (1992), Abstract.

Wootton, J.H., et al., "Endocervical ultrasound applicator for integrated hyperthermia and HDR brachytherapy in the treatment of locally advanced cervical carcinoma", Med. Phys. 38(2), Feb. 2011, pp. 598-612.

Diederich C.J., et al., "Catheter-based ultrasound hyperthermia with HDR brachytherapy for treatment of locally advanced cancer of the prostate and cervix", Proc. SPIE7901, Energy-based Treatment of Tissue and Assessment VI (2011), Abstract.

Venselaar, J., et al., (edited), "A Practical Guide to Quality Control of Brachytherapy Equipment", European Guidelines for Quality Assurance in Radiotherapy, Booklet No. 8, ISBN 90-804532-8 (2004).

SYSTEM FOR APPLYING RADIATION TO A TARGET REGION WITHIN A SUBJECT

CROSS-REFERENCE TO PRIOR APPLICATIONS

This application is the U.S. National Phase application under 35 U.S.C. § 371 of International Application Serial No. PCT/EP2015/053962, filed on Feb. 26, 2015, which claims the benefit of European Patent Application No. 14193853.0, filed on Nov. 19, 2014 and European Patent Application No. 14156948.3, filed on Feb. 27, 2014. These applications are hereby incorporated by reference herein.

FIELD OF THE INVENTION

The invention relates to a system, method and computer program for applying radiation to a target region within a subject.

BACKGROUND OF THE INVENTION

A system for applying radiation to a target region within a subject is, for instance, a high dose rate (HDR) brachytherapy system. An HDR brachytherapy system comprises a brachytherapy catheter which is introduced into the target region, wherein within the brachytherapy catheter a radioactive radiation source is moved to different dwell positions at which the radioactive radiation source is located for respective dwell times. The target region is treated by radioactive radiation emitted by the radioactive radiation source at the different dwell positions for the respective dwell times.

The radiation emitted by the radiation source destroys, for instance, cancerous tissue primarily through the generation of oxygen radicals that attack the tumor DNA Cells to be destroyed may only contain a relatively low amount of oxygen, which may lead to a reduced effectiveness of the application of the radiation.

SUMMARY OF THE INVENTION

It is an object of the present invention to provide a system, method and computer program for applying radiation to a target region within a subject, wherein the effectiveness of the application of the radiation can be improved.

In a first aspect of the present invention a system for applying radiation to a target region within a subject is presented, wherein the system comprises:
- an elongated introduction element for being inserted into the subject and for introducing a radiation source emitting radiation to be applied to the target region into the subject,
- a moving unit for moving the radiation source within the introduction element such that the radiation source is located within or close to the target region,
- a heating unit for heating the target region,
- a temperature determination unit for determining the temperature along the length of the introduction element, and
- a control unit for controlling the moving unit depending on the determined temperature.

The susceptibility of the subject for the radiation emitted by the radiation source at a respective location along the length of the introduction element can depend on the temperature at the respective location. For instance, if the subject is a living being like a person or an animal, the applied radiation can be more effective, if the irradiated region has an increased oxygen level, wherein such an increased oxygen level can be achieved by heating, because this will lead to a higher blood circulation and oxygen supply. Thus, determining the temperature along the length of the introduction element and controlling the movement of the radiation source within the introduction element depending on the determined temperature allows for an optimized effect of the application of the radiation.

The heating unit may be adapted to heat the target region by microwave, radiofrequency and/or ultrasound. The introduction element is preferentially an elongated hollow introduction element like a catheter or needle, especially a brachytherapy catheter. The system is preferentially adapted to perform an HDR therapy, while the target region is heated and/or after the target region has been heated.

In an embodiment the control unit is adapted to control the moving unit such that the radiation source is moved to and stopped at a location within the subject, at which the determined temperature is larger than a predefined threshold temperature. Such a control of the movement of the radiation source within the introduction element depending on the determined temperature can lead to a further improved effectiveness of the application of the radiation to the target region.

Moreover, the system may comprise a target region providing unit for providing the position of the target region within the subject, wherein the temperature determination unit may be adapted to determine a temperature within the target region based on the temperature determined along the length of the introduction element and the provided target region and wherein the control unit may be adapted to control the moving unit such that the radiation source is not introduced into the subject or retracted from the subject, if the determined temperature within the target region is below a predefined threshold temperature. In particular, therapy delivery may be stopped, if the target region is not in hyperthermia. The determined temperature within the target region may be, for instance, an average of the temperatures along the length of the introduction element, which are within the target region, a minimum of these temperatures, a maximum of these temperatures, et cetera. In an embodiment the control unit may be adapted to control the moving unit such that the radiation source is not introduced into the subject or retracted from the subject, if a single, a predefined amount or all of the temperatures along the length of the introduction element, which are within the target region, are below the predefined threshold temperature. Furthermore, the system may comprise an output unit for outputting an alarm, if the determined temperature within the target region is below a predefined threshold temperature, i.e., for instance, an alarm may be generated, if the target region is not in hyperthermia. The user may then stop the application of the radiation to the target region by removing the radiation source from the subject, thereby ensuring that the radiation is applied to the subject, especially the target region, only if the radiation is very effective.

In an embodiment the system comprises a target region providing unit for providing the position of the target region within the subject and a plan generation unit for generating a plan defining dwell positions and dwell times of the radiation source within the subject based on the provided position of the target region within the subject and the determined temperature, wherein the control unit is adapted to control the moving unit in accordance with the generated plan. The generation of the plan can also include an adaptation of an existing plan. The adaptation may be performed even during therapy delivery. The plan generation unit may be adapted to generate the plan such that it defines dwell positions only at locations within the subject, at which the determined temperature is larger than a predefined threshold temperature. Moreover, the plan generation unit may be adapted to generate the plan such that a dwell time at a dwell position depends on the temperature at the dwell position. For instance, if at a location within the target region the temperature is higher than a threshold temperature such that an increased oxygen level can be assumed, but if the temperature is still relatively low, the dwell time may be larger, whereas, if the temperature is larger, the dwell time may be smaller at this location. Generating the plan not only depending on, for instance, the position of the target region, but also on the current temperature distribution within the target region, can further improve the effectiveness of the application of the radiation to the target region.

In a preferred embodiment the introduction element comprises an optical fiber arranged along the length of the introduction element for generating optical signals which are indicative of the temperature along the length of the introduction element, wherein the temperature determination unit is adapted to determine the temperature along the length of the introduction element based on the generated optical signals. The optical fiber preferentially comprises Bragg gratings for generating the optical signals. Alternatively or in addition, the temperature determination unit can be adapted to determine the temperature along the introduction element in another way. For instance, an image based temperature measuring technique can be used for determining the temperature along the length of the introduction element. In particular, a magnetic resonance or ultrasound thermometry technique may be used for determining the temperature along the length of the catheter. In an embodiment the position of the introduction element in an image is determined by segmentation and the temperature along the length of the introduction element is determined based on the image values at the determined position of the introduction element. The system may further comprise a position determination unit for determining the position of the introduction element, especially based on the optical signals. Moreover, the plan generation unit may be adapted to generate a plan defining dwell positions and dwell times of the radiation source within the subject based on a provided position of the target region within the subject, the determined temperature and the determined position of the introduction element, wherein the control unit may be adapted to control the moving unit in accordance with the generated plan. Determining the position of the introduction element based on the optical signals, especially based on generated optical shape sensing signals, allows for a very accurate determination of the position of the introduction element within the subject, wherein this very accurately determined position can be used, in order to initially generate or adapt a plan defining dwell positions and dwell times of the radiation source, especially in real-time. This can lead to a further increased effectiveness of the application of the radiation to the target region. However, the position determination unit can also be adapted to determine the position of the introduction element in another way, for instance, by using an electromagnetic tracking technique, an ultrasound tracking technique, et cetera. In an embodiment the system comprises an image providing unit for providing an image of the subject showing at least the target region, and an output unit comprising a display for displaying the image overlaid with a representation of the introduction element based on the determined position of the introduction element. This allows a user to check whether the introduction element is at a desired position within the subject.

The target region providing unit may be adapted to determine the position of the target region based on the provided image of the subject. For instance, the target region providing unit may be adapted to segment the target region in the provided image, in order to determine the position of the target region.

The output unit may be adapted to output a single value depending on the determined temperature. The single value may be a minimum value, a maximum value or an average value, especially within the target region. Moreover, the system may comprise several introduction elements for being inserted into the subject and for introducing a radiation source into the subject, wherein the temperature may be determined along the lengths of the introduction elements by using, for instance, optical fibers arranged along the lengths of the introduction elements, in order to determine a three-dimensional temperature distribution within the subject based on the optical signals.

In an embodiment the system comprises an image providing unit for providing an image of the subject showing at least the target region, wherein the temperature determination unit is adapted to determine a first temperature along the length of the introduction element based on the optical signals and to determine a second temperature based on the provided image by using an image-to-temperature transformation process, wherein the image-to-temperature transformation process is calibrated by using the first temperature. The image providing unit may include an ultrasound imaging device or magnetic resonance imaging device. Thus, the temperature, which is obtained based on, for instance, the optical signals, can be used to calibrate another, image-based temperature measurement procedure, wherein, after this calibration has been performed, the temperature obtained from the image-based temperature measuring procedure can be used for determining the temperature within, for example, the target region. This additional temperature information can be, for instance, shown on a display and/or used by the control unit for controlling the moving unit, which may lead to a further improved effectiveness of applying the radiation to the target region. In particular, the temperature determined along the length of the introduction element may directly be used for controlling the moving unit and/or the temperature determined along the length of the introduction element may indirectly be used for controlling the moving unit, wherein in the latter case the temperature along the length of the introduction element may be used for calibrating the image-to-temperature transformation and a temperature, for instance, within the target region, may be determined based on the calibrated image-to-temperature transformation.

The temperature determination unit may be adapted to determine the temperature along the entire length of the introduction element or along a part of the length of the introduction element. In the latter case the temperature may be determined along a part of the length of the introduction element which is arranged within the target region.

The system preferentially further comprises a control unit for controlling the heating unit depending on the determined temperature. For instance, the heating unit can be controlled such that the target region, especially the entire target region, has a temperature being larger than a predefined threshold temperature, in order to ensure that the target region is in a hyperthermia condition, when placing the radiation source within or close to the target region. This can lead to a further improved effectiveness of applying the radiation to the target region.

In a further aspect of the present invention a method for applying radiation to a target region within a subject is presented, wherein the method comprises:
heating the target region by using a heating unit,
determining a temperature along a length of an elongated introduction element, which has been inserted into the subject for introducing a radiation source emitting radiation to be applied to the target region into the subject, by a temperature determination unit, and
controlling a moving unit for moving the radiation source within the introduction element such that the radiation source is located within or close to the target region depending on the determined temperature by a control unit.

In a further aspect of the present invention a computer program for applying radiation to a target region within a subject is presented, wherein the computer program comprises program code means for causing a system as defined in claim 1 to carry out the steps of the method as defined in claim 14, when the computer program is run on a computer controlling the system.

It shall be understood that the system of claim 1, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings.

DETAILED DESCRIPTION OF EMBODIMENTS

Figure 1:
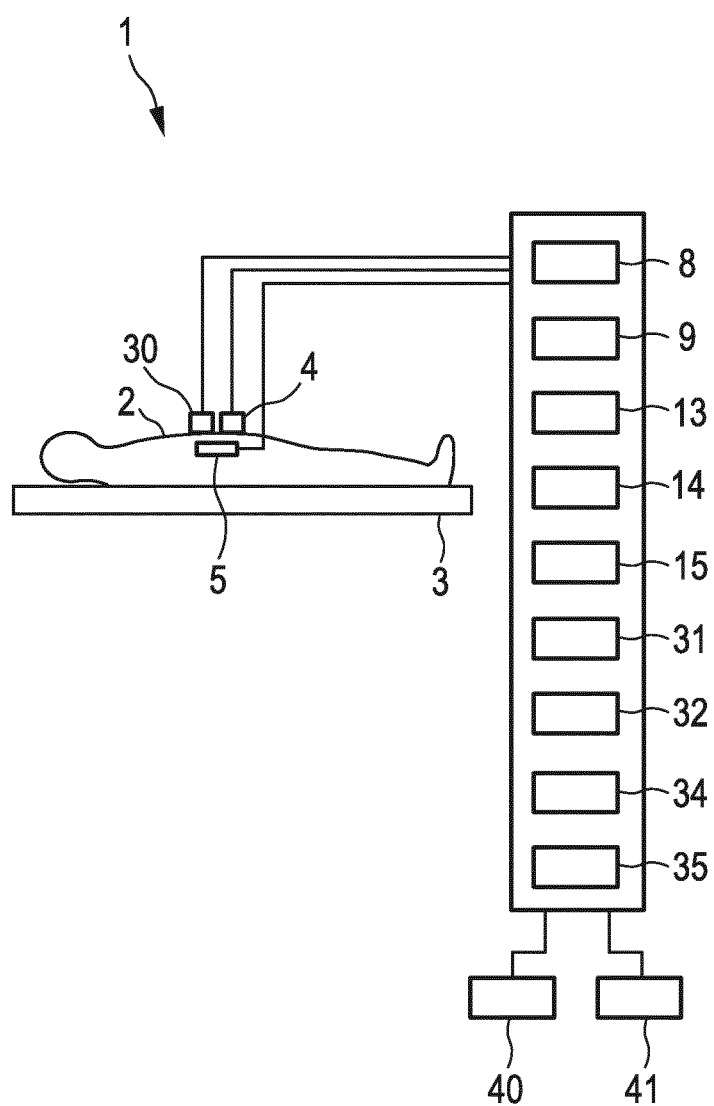
FIG. 1 shows schematically and exemplarily an embodiment of a system for applying radiation to a target region within a subject.
Figure 2:
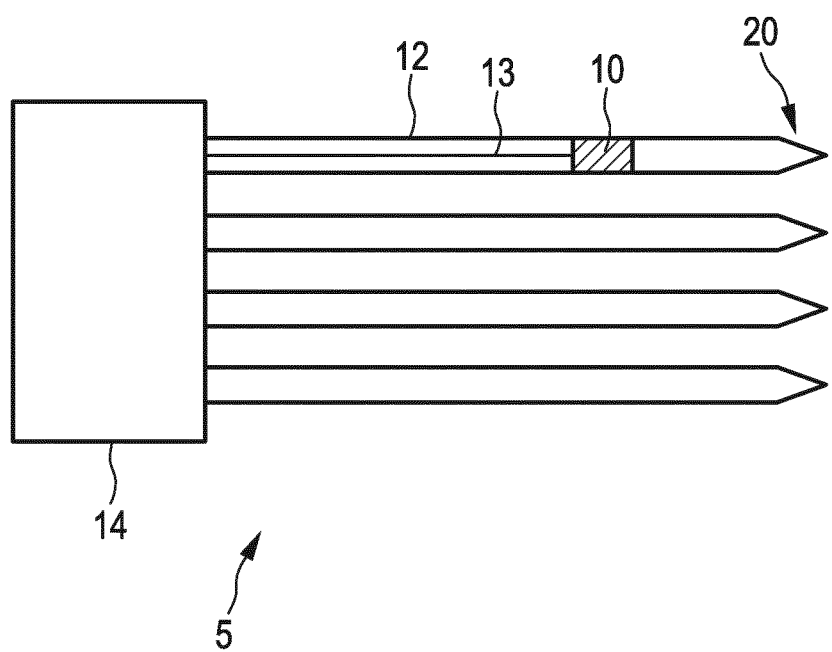
FIG. 2 shows schematically and exemplarily introduction elements of the system to be inserted into the subject for applying the radiation to the target region.

FIG. 1 shows schematically and exemplarily a system for applying radiation to a target region within a subject. In this embodiment the system 1 is a brachytherapy system for applying a brachytherapy to a subject 2 lying on a support means 3 like a table. The brachytherapy system 1 comprises a placing unit 5 for placing a radiation source close to or within a target region within the subject 2 for directing radiation emitted by the radiation source to the target region. The radiation source 10 is preferentially a radioactive radiation source emitting radioactive radiation like Ir-192. The placing unit 5 is exemplarily and schematically shown in more detail in FIG. 2.

The placing unit 5 comprises several elongated introduction elements 12, which in this embodiment are catheters, with tips 20 for being introduced into the subject 2. The placing unit 5 further comprises a drive wire 13 to which the radiation source 10 is attached, wherein the drive wire 13 with the radiation source 10 can be moved within each of the catheters 12 for placing the radiation source 10 at desired dwell positions for desired dwell times. The placing unit 5 further comprises a moving unit 14, which may also be regarded as being an afterloader and which is adapted to introduce the radiation source 10 into and to move the radiation source 10 within the different catheters 12 by using a motor. In particular, the moving unit 14 may be adapted to drive the radiation source 10 through an indexer that connects with the different catheters 12. For more details regarding this kind of placing the radiation source 10 within the subject reference is made to the "A Practical Guide to Quality Control of Brachytherapy Equipment" edited by J. Venselaar and J. Perez-Calatayud, European Society for Therapeutic Radiology and Oncology (2004), which is herewith incorporated by reference.

The placing unit can comprise further elements for assisting in placing the radiation source at the desired dwell positions for the desired dwell times within the subject 2. For instance, the placing unit can comprise a template which can be used for inserting the catheters in a more uniform configuration into the subject 2.

Figure 3:
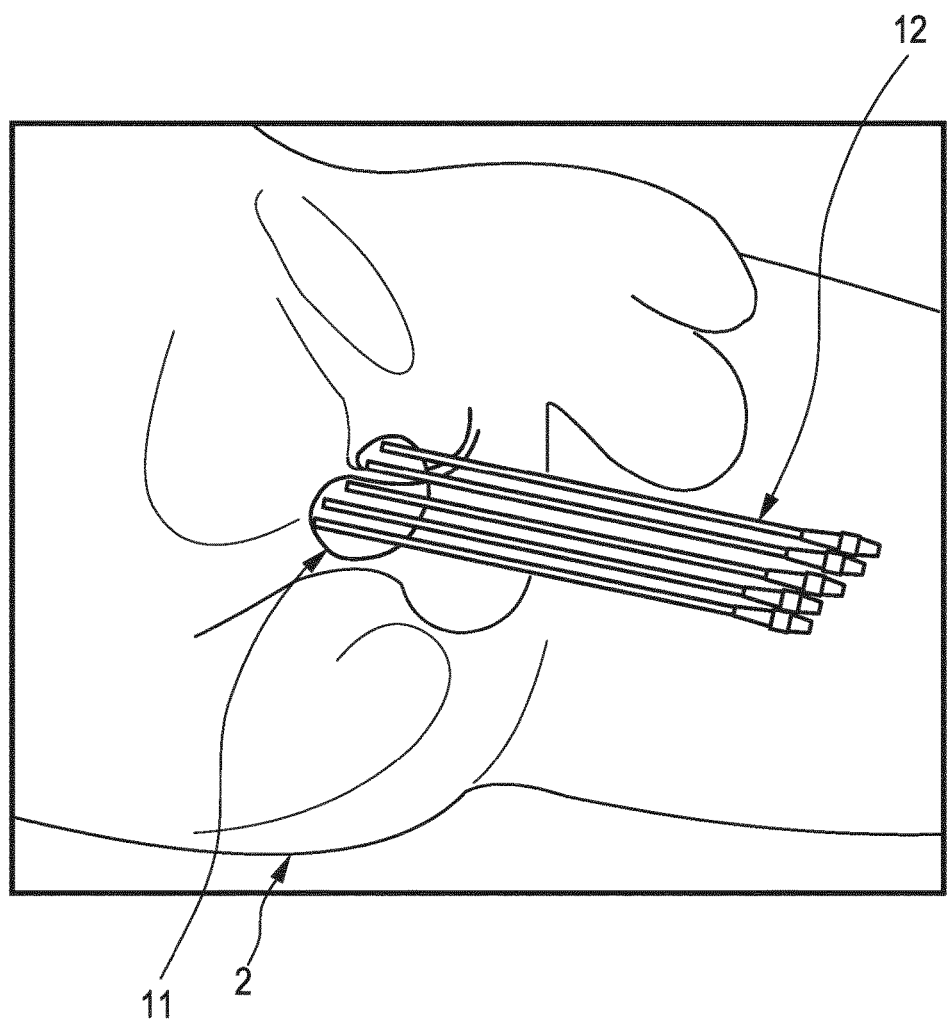
FIG. 3 illustrates schematically and exemplarily a possible arrangement of the introduction elements after having been inserted into the subject.

In this embodiment the system 1 is adapted to treat a target region, which is preferentially a tumor region, in a prostate. The radiation source may be placed within the target region and/or close to the target region, i.e., in particular, adjacent to the target region. FIG. 3 shows schematically and exemplarily a possible arrangement of the catheters 12 of the placing unit 5 within the prostate 11.

Figure 4:
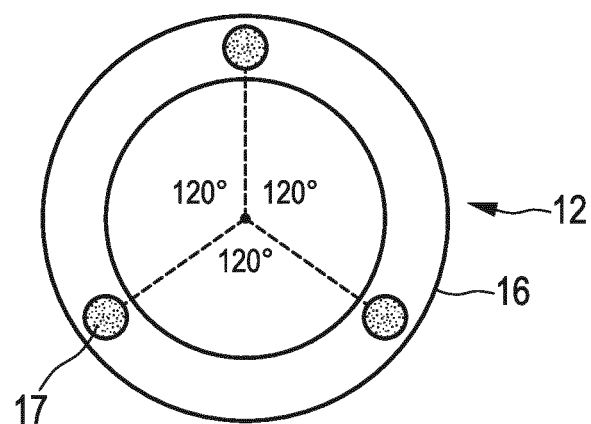
FIG. 4 shows schematically and exemplarily a sectional view of an introduction element.

Each catheter 12 comprises an optical fiber with Bragg gratings. In particular, as schematically and exemplarily shown in FIG. 4, each catheter 12 may comprise three optical fibers 17 with Bragg gratings within an outer wall 16, wherein these three optical fibers 17 may be angularly equidistantly distributed, i.e. they may have an angular distance to each other of 120 degrees. The system 1 further comprises an optical sensing control unit 9 for generating optical signals, which are indicative of the temperature along the respective catheter 12 and the position of the respective catheter 12 within the subject, by using the optical fibers 17 with the Bragg gratings.

For instance, each optical fiber 17 may comprise ten Bragg gratings with a length of 8 mm and separated by a distance of 20 mm along the respective optical fiber 17. The optical fibers 17 may be connected to a broadband source and a detector of the optical sensing control unit 9. The peak reflected wavelength for each Bragg grating shifts due to changes in strain and temperature such that these shifts can be used to reconstruct the shape of and temperature along the respective catheter 12. In particular, the shape of the entire respective catheter 12 relative to a respective known anchoring location can be reconstructed, in order to determine the position of each portion or section of the respective catheter 12, and the temperature at different portions or sections along the length of the respective catheter 12 can be determined. For example, the shift $\Delta\lambda_B$ of a peak reflected wavelength $\lambda_B$ depending on a strain $\varepsilon$ and a temperature change $\Delta T$ can be given by $$\Delta\lambda_B/\lambda_B = k_S \varepsilon + k_T \Delta T \quad (1)$$

wherein $k_S$ and $k_T$ denote constants, which can be determined by calibration measurements, and wherein this equation can be used together with the knowledge that the three optical fibers 17 of a same catheter 12 have an angular distance of 120 degrees to each other for determining the shape of the respective catheter 12 and the temperature along the length of the respective catheter 12. The temperature between the different portions or sections, at which the temperature has been determined, may be determined by interpolation. For more details regarding the determination of the shape and hence position of the respective catheter 12 and of the temperature along the length of the respective catheter 12 based on the optical signals reference is made to, for instance, "Fiber Optic Sensors" by F. T. S. Yu et al., Marcel Dekker Inc., (2002), especially chapter 4 of this book, which is herewith incorporated by reference. The determination of the temperature along the length of the respective catheter 12 is performed by a temperature determination unit 13 and the shape and hence the position of the respective catheter 12 is determined by a position determination unit 35.

The system 1 further comprises an imaging unit 4, 8 being, in this embodiment, an ultrasound unit. The ultrasound unit comprises an ultrasound probe 4 and an ultrasound control unit 8. The ultrasound probe 4 may be placed on the outside surface of the subject 2 as schematically and exemplarily illustrated in FIG. 1, or the ultrasound probe may be arranged within the subject 2, in order to generate an image of the subject 2, especially of the target region. For instance, the ultrasound probe may be a transrectal ultrasound probe. The generated image can be shown to a user on a display 41, in order to guide the user while introducing the catheters 12 into the subject 2. In another embodiment the imaging unit can be another kind of imaging device like a magnetic resonance imaging device. Since the imaging unit 4, 8 provides the image showing the subject 2 including the target region, the imaging unit 4, 8 can be regarded as being an image providing unit.

In an embodiment the positions of the catheters 12 within the subject 2 determined by the position determination unit 35 can be registered with the image of the subject provided by the imaging unit 4, 8, in order to allow the display 41 to show representations of the catheters 12 within the image based on the determined positions of the catheters 12. Moreover, a target region providing unit 32 can be adapted to determine the position of the target region within the subject 2 based on the image provided by the imaging unit 4, 8, for instance, by segmenting the target region within the provided image. Based on the determined position of the target region within the subject 2, a representation of this target region may be shown on the display 41. In this way the display 41 can guide the user while introducing the catheters 12 into the subject 2.

Instead of or in addition to generating a current image of the subject 2, the imaging unit can be adapted to provide a pre-interventional image, wherein also in this case the determined positions of the catheters 12 within the subject 2 can be registered with the image of the subject 2 provided by the imaging unit, in order to allow the display 41 to show a representation of the catheters 12 overlaid with the provided image. For registering the determined positions of the catheters 12 with the provided image known registration techniques can be used, which may be based on detecting a catheter equipped with an optical fiber with Bragg gratings in an image generated by the imaging unit, while the position of the catheter is determined based on the optical signals.

The system 1 further comprises a heating unit 30 for heating the target region. For instance, the heating unit may be adapted to heat the target region by using an ultrasound technique, a microwave technique or a radiofrequency technique. In particular, the heating unit may be adapted to perform a transurethral microwave heating or a high-intensity focused ultrasound (HIFU) heating, wherein ultrasound beams may be focused to a small focal zone, which may be located at the target region, by using a curved transducer or a phased array. For more details regarding the HIFU heating reference is made to, for instance, the article "HIFU for palliative treatment of pancreatic cancer" by T. Khokhlova and J. Hwang, volume 2, number 3, pages 175 to 184, Journal of Gastrointestinal Oncology (2011), which is herewith incorporated by reference. In an embodiment the ultrasound unit for generating ultrasound images may be integrated with an ultrasound-based heating unit. However, as schematically illustrated in FIG. 1, the ultrasound unit for generating ultrasound images and the ultrasound-based heating unit can also be separate units.

The system further comprises a brachytherapy control unit 15 for controlling the moving unit 14 depending on the determined temperature. The control unit 15 is preferentially further adapted to control the moving unit 14 depending on the provided position of the target region. In particular, the brachytherapy control unit 15 is adapted to control the moving unit 14 such that the radiation source 10 is moved to and stopped at a location within or close to, i.e. adjacent to, the target region, at which the determined temperature is larger than a predefined threshold temperature. This threshold temperature is preferentially predefined such that the target region is in a hyperthermia condition at the location within or close to the target region, in order to increase the effectiveness of applying the radiation to the target region. A location close to the target region is preferentially an adjacent or surrounding location which is close enough for allowing the radiation emitted by the radiation source to treat the target region.

The brachytherapy control unit 15 is preferentially adapted to control the moving unit 14 such that the radiation source 10 is not introduced into the subject 2 or retracted from the subject 2, if the temperature of the target region, which might be an average temperature of all temperatures measured within the target region, is below a predefined threshold temperature. This threshold temperature may be predefined such that, if the target region has a temperature being larger than the threshold temperature, the target region is in a hyperthermia condition. Moreover, in an embodiment the brachytherapy control unit 15 may be adapted to not introduce the radiation source into the subject 2 or to retract the radiation source 10 from the subject 2, if at each location within the target region, at which the temperature is measured, the temperature is below the predefined threshold temperature. As a threshold temperature 40 degree Celsius or a larger temperature may be used. In an embodiment the heating unit 30 may be controlled such that the target region should have a temperature within a range of 40 to 45 degree Celsius, wherein especially in this case the threshold temperature might be 40 degree Celsius.

Furthermore, the display 41 or another output unit like an acoustic output unit may be adapted to output an alarm, if among the temperatures determined within the target region at least one temperature is below a predefined threshold temperature and/or if the average temperature of the target region is below the predefined threshold temperature. Moreover, in an embodiment, if the radiation source is located at a certain dwell position within the subject 2, especially close to or within the target region, and if the temperature at this dwell position is smaller than the threshold temperature, the alarm may be output.

The brachytherapy control unit 15 may be adapted to control the moving unit 14 in accordance with a plan defining dwell positions and dwell times of the radiation source 10 within the subject 2, wherein this plan may have been generated by a plan generation unit 31. The plan generation unit 31 may be adapted to generate the plan based on the provided position of the target region, the determined temperature along the length of the catheters 12 and the determined positions of the catheters 12. The plan generation unit 31 may be adapted to initially generate the plan and/or to generate the plan by adapting an existing plan. In particular, the plan may be adapted in real-time based on a current temperature along the catheters 12 and/or current positions of the catheters 12 and/or a current position of the target region. The brachytherapy control unit 15 can be adapted to move the radiation source 10 in accordance with the real-time adapted plan defining optimized dwell positions and dwell times. The plan generation unit 31 can be adapted to generate the plan such that it defines dwell positions only in regions within or close to the target region, in which the determined temperature is larger than the predefined threshold temperature. Moreover, the plan generation unit 31 can be adapted to generate the plan such that a dwell time at a dwell position depends on the temperature at the dwell position. Generally, the plan generation unit 31 can comprise plan generation rules defining dwell positions and dwell times depending on the position of the target region, the positions of the catheters and the temperature along the catheters.

The system 1 further comprises a heating control unit 34 for controlling the heating unit 30 depending on the determined temperature. For instance, the control unit 34 may control the heating unit 30 such that at least at dwell positions defined by the plan generated by the plan generation unit the temperature is larger than the predefined threshold temperature. In particular, the heating control unit 34 can be adapted to control the heating unit 30 such that all temperatures determined along the catheters 12, which have been determined for locations being within the target region, are larger than the predefined threshold temperature.

The system 1 further comprises an input unit 40 like a keyboard, a computer mouse, a touch pad, et cetera, in order to allow the user to, for instance, input commands into the system 1 like a start command for starting a brachytherapy procedure, a stop command for stopping a brachytherapy procedure, et cetera. The input unit 40 may also be used to input parameters defining the brachytherapy procedure like dwell positions and dwell times.

Figure 5:
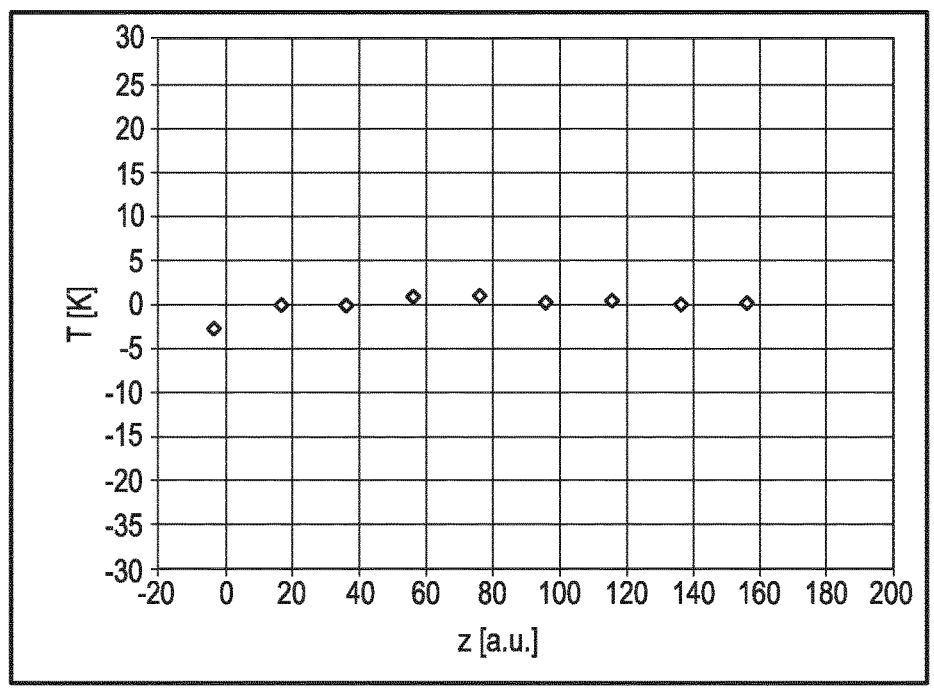
FIG. 5 shows schematically and exemplarily a visualization of temperatures determined at different locations along a length of an introduction element.

The display 41 may be adapted to display a single temperature value for the entire target region. For instance, a minimum temperature value, a maximum temperature value or an average temperature value may be determined for the target region based on all temperatures determined for locations along the catheters 12, which are within the target region, and the minimum temperature value, the maximum temperature value or the average temperature value may be shown on the display 41. However, it is of course also possible that, for instance, a chart showing the temperature values along the length of a catheter is displayed as schematically and exemplarily illustrated in FIG. 5. FIG. 5 shows a relative temperature T in Kelvin for different locations z in arbitrary units along a catheter. The z locations schematically and exemplarily illustrated in FIG. 5 correspond to different locations of Bragg gratings along the respective catheter. Temperature values for locations in between the locations shown in FIG. 5 can be determined by, for instance, interpolation. The temperatures determined for the locations, at which the Bragg sensors, i.e. the Bragg gratings, are present and the interpolated temperatures for intermediate locations can be used, for instance, by the plan generation unit 31 for generating a plan defining dwell positions and dwell times, wherein the brachytherapy control unit 15 may control the moving unit 14 in accordance with the plan, in order to indirectly, i.e. via the plan, control the moving unit 14 depending on the temperatures, and/or the temperatures may be directly used by the brachytherapy control unit 15 for controlling the moving unit for moving the radiation source within the catheters depending on the temperatures along the lengths of the catheters and/or the temperature may be used by the heating control unit 34 for controlling the heating unit 30 depending on the temperatures along the lengths of the catheters. Also a two-dimensional or a three-dimensional temperature map may be determined based on the temperatures along the lengths of the different catheters.

Figure 6:
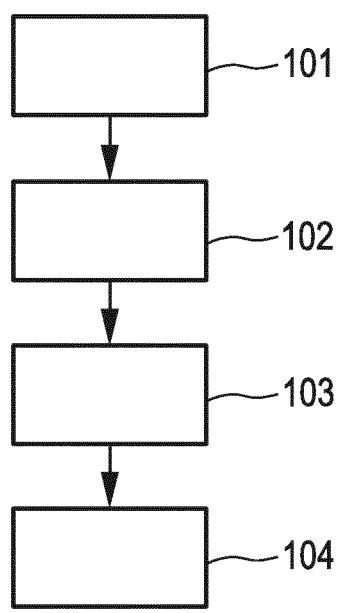
FIG. 6 shows a flowchart exemplarily illustrating an embodiment of a method for applying radiation to a target region within a subject.

The temperature determination unit 13 can be adapted to use the temperature determined along the lengths of the catheters 12 for calibrating an image-to-temperature transformation process, which may be applied to an image generated by the imaging unit 4, 8. For instance, the imaging unit 4, 8 can be adapted to use ultrasound thermometry, wherein an ultrasound image is transformed into a temperature distribution. This ultrasound thermometry technique can be calibrated by determining the temperature of the subject by using ultrasound thermometry, while the temperature is known from the optical-signals-based temperature determination. In another embodiment also another image-based temperature determination technique like a magnetic-resonance-image-based temperature determination technique can be calibrated by using the temperatures determined along the catheters based on the optical signals. The temperatures determined by the calibrated image-based temperature determination techniques may then also be shown on the display 41 and used by the plan generation unit 31, the brachytherapy control unit 15 and/or the heating control unit 34. In the following an embodiment of a method for applying radiation to a target region within a subject will exemplarily be described with reference to a flowchart shown in FIG. 6.

After the catheters 12 have been inserted into the subject 2 such that they are close to or within the target region and before or during introducing the radiation source 10 through a catheter 12 into the subject 2 such that it is located close to or within the target region, in step 101 the target region is heated by using the heating unit 30. In step 102 optical signals are generated, which are indicative of the temperature along the lengths of the catheters 12, by using the optical fibers 17 arranged along the lengths of the catheters 12, wherein in step 103 the temperature along the lengths of catheters 12 is determined based on the optical signals by the temperature determination unit 13. In step 104 the moving unit 14 is controlled by the brachytherapy control unit 15 depending on the determined temperature such that the radiation source 10 is moved to a location within or close to the target region. At least steps 102 to 104 may be carried out in a loop such that the temperature is continuously measured and the movement of the radiation source within the catheters is controlled depending on the currently present temperature, i.e. temperature distribution, along the lengths of the catheters.

Hyperthermia is a type of cancer treatment in which body tissue is exposed to high temperatures, i.e., for instance, to temperatures within a range of 40 to 45 degrees Celsius, in order to damage and kill cancer cells. Hyperthermia can be applied to a relatively small area such as a tumor region, wherein a technique may be used, which delivers energy to heat the tumor region like a microwave technique, a radiofrequency technique or an ultrasound technique. Radiation therapy is another type of cancer treatment, in which ionizing radiation is used to control or kill malignant cells. The ionizing radiation can be administered using external beam radiation therapy (EBRT), permanent interstitial sources (low dose rate brachytherapy) or temporary interstitial sources (HDR brachytherapy).

Hyperthermia and radiation therapy complement each other. Ionizing radiation destroys cancerous tissue primarily through the generation of oxygen radicals that attack the tumor DNA. Thus, tumor cells containing an insufficient oxygen level are relatively resistant to ionizing radiation. A radiation therapy is more effective in well-oxygenated tumors such that hyperthermia, which leads to an improved blood circulation and hence to an improved oxygen supply, improves the effectiveness of the radiation therapy. In addition, hyperthermia can also cause an accumulation of proteins in the cell nucleus, thereby preventing a self-repair of cancer cell DNA. Finally, ionizing radiation and hyperthermia damage cells during different phases of the cell cycle. During the synthesis phases, tumor cells are resistant to ionizing radiation, but susceptible to the destructive effects of hyperthermia. Combining hyperthermia and radiation therapy can therefore improve a cancer therapy. In particular, hyperthermia can be regarded as being a very effective potentiator of radiation therapy.

The system described above with reference to FIGS. 1 to 5 is adapted to monitor the temperature in the target region, especially in tumor tissue, during radiation therapy. Showing the determined temperatures on the display, i.e. reporting the temperature measured along the catheters to a clinical user, provides a quality assurance for the combination therapy. However, the monitored temperature can also be used to provide a temperature-based adaptation and/or generation of radiation therapy plans, especially as described above. In particular, the temperature measurements may be used as an input for planning a radiation therapy, in order to confine the treatment only to susceptible areas and/or to adapt the radiation dose, i.e. the dwell times, based on the respective local temperature.

The radiation source, which is preferentially a highly radioactive source and which is preferentially used to perform an HDR brachytherapy, traverses the catheters positioned in and/or around the target region, in order to deliver ionizing radiation. Dedicated temperature sensing needles or catheters would either be positioned too far from the target region and/or block potential locations for treatment delivery catheters. The temperature sensing functionality is therefore preferentially integrated in the catheters. Moreover, the temperature sensing in the catheters is preferentially combined with tracking/navigation technology, for instance, by using an optical shape sensing technology as described above.

The system can be adapted to raise an alarm, if the target region is no longer in hyperthermia, wherein the alarm may be a visible alarm, an audible alarm, a tactile alarm, et cetera. Moreover, the system can be adapted to stop therapy delivery, if the target region is no longer in hyperthermia. Furthermore, based on the measured temperature in the target region the system may modify the therapy delivery. For instance, the moving unit, which may be regarded as being an afterloader, can be instructed by the brachytherapy control unit to shorten or lengthen dwell times at certain dwell positions based on the measured temperature. This adaptation of the therapy delivery can be an automatic procedure. Moreover, also an interactive procedure can be provided, in which the user is informed about the temperature in the target region, whereupon the user may modify the therapy delivery, especially a radiation therapy plan defining dwell positions and dwell times, based on the information about the temperature in the target region. For instance, based on the temperature in the target region, the user can be allowed to decide on a continuation of the treatment, i.e. of the heating of the target region and/or the introduction of the radiation source into or close to the target region. This may prevent unnecessary pain which may be induced by, for instance, temperature elevation.

Although in above described embodiments the optical fibers of the catheters comprise discrete Bragg gratings, which are used for generating optical signals, which in turn are used to reconstruct the shape and hence the position of the respective catheter and to determine the temperature along the length of the respective catheter, in other embodiments instead of using optical fibers with discrete Bragg gratings alternative fiber optic approaches may be used like the use of continuous gratings.

Although in above described embodiments the introduction element is a catheter, in other embodiments the introduction element can also be another introduction element for being introduced into the subject. Moreover, although in above described embodiments several introduction elements have been inserted into the subject, in other embodiments only a single introduction element may be inserted into the subject. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the determination of a temperature along an introduction element, the determination of a position of an introduction element, the determination of a target region within a subject, the generation of a plan defining dwell positions and dwell times, et cetera and/or the control of the system for applying radiation to a target region within a subject, which have been described as being performed by a certain number of units or devices, can be performed by any other number of units or devices. For instance, the determination of the temperature along the introduction element, the determination of the position of the introduction element within the subject, the determination of the position of the target region within the subject, the generation of the plan defining dwell positions and dwell times and other procedures can be performed by a single processing unit. These operations and/or the control of the system for applying radiation to a target region within a subject in accordance with the method for applying radiation to a target region within a subject can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a system for applying radiation to a target region within a subject. An introduction element like a brachytherapy catheter is inserted into the subject and a radiation source is moved within the introduction element such that it is located within or close to the target region. The target region is heated, wherein the movement of the radiation source within the introduction element is controlled depending on the temperature along the introduction element. The susceptibility of the subject for the radiation emitted by the radiation source at a respective location along the length of the introduction element can depend on the temperature at the respective location such that by controlling the movement of the radiation source depending on the temperature along the length of the introduction element the application of the radiation can be optimized.

The invention claimed is:

1. A system for applying radiation to a target region within a subject, wherein the system comprises:
   an elongated introduction element for being inserted into the subject and for introducing a radiation source emitting radiation to be applied to the target region into the subject,
   a moving unit for moving the radiation source within the introduction element such that the radiation source is located within or close to the target region,
   a heating unit for heating the target region,
   a temperature determination unit for determining the temperature along the length of the introduction element, and
   a control unit for controlling the moving unit depending on the determined temperature.

2. The system as defined in claim 1, wherein the control unit is adapted to control the moving unit such that the radiation source is moved to and stopped at a location within the subject, at which the determined temperature is larger than a predefined threshold temperature.

3. The system as defined in claim 1, wherein the system further comprises a target region providing unit for providing the position of the target region within the subject, wherein the temperature determination unit is adapted to determine a temperature within the target region based on the temperature determined along the length of the introduction element and the provided target region and wherein the control unit is adapted to control the moving unit such that the radiation source is not introduced into the subject or retracted from the subject, if the temperature within the target region is below a predefined threshold temperature.

4. The system as defined in claim 1, wherein the system further comprises a target region providing unit for providing the position of the target region within the subject, wherein the temperature determination unit is adapted to determine a temperature within the target region based on the temperature determined along the length of the introduction element and the provided target region, wherein the system further comprises an output unit for outputting an alarm, if the temperature within the target region is below a predefined threshold.

5. The system as defined in claim 1, wherein the system further comprises a target region providing unit for providing the position of the target region within the subject and a plan generation unit for generating a plan defining dwell positions and dwell times of the radiation source within the subject based on the provided position of the target region within the subject and the determined temperature, wherein the control unit is adapted to control the moving unit in accordance with the generated plan.

6. The system as defined in claim 5, wherein the plan generation unit is adapted to generate the plan such that it defines dwell positions only at locations within the subject, at which the determined temperature is larger than a predefined threshold temperature.

7. The system as defined in claim 5, wherein the plan generation unit is adapted to generate the plan such that a dwell time at a dwell position depends on the temperature at the dwell position.

8. The system as defined in claim 1, wherein the introduction element comprises an optical fiber) arranged along the length of the introduction element for generating optical signals, which are indicative of the temperature along the length of the introduction element and wherein the temperature determination unit is adapted to determine the temperature along the length of the introduction element based on the generated optical signals.

9. The system as defined in claim 8, wherein the system further comprises a position determination unit for determining the position of the introduction element based on the optical signals.

10. The system as defined in claim 8, wherein the system comprises an image providing unit for providing an image of the subject showing at least the target region, wherein the temperature determination unit is adapted to determine a first temperature along the length of the introduction element based on the optical signals and to determine a second temperature based on the provided image by using an image-to-temperature transformation process, wherein the image-to-temperature transformation process is calibrated by using the first temperature.

11. The system as defined in claim 1, wherein the system further comprises a position determination unit for determining the position of the introduction element, a target region providing unit for providing the position of the target region within the subject and a plan generation unit for generating a plan defining dwell positions and dwell times of the radiation source within the subject based on the provided position of the target region within the subject, the determined temperature and the determined position of the introduction element, wherein the control unit is adapted to control the moving unit in accordance with the generated plan.

12. The system as defined in claim 1, wherein the system further comprises a position determination unit for determining the position of the introduction element, an image providing unit for providing an image of the subject showing at least the target region and an output unit comprising a display for displaying the image overlaid with a representation of the introduction element based on the determined position of the introduction element.

13. The system as defined in claim 1, wherein the system further comprises a control unit for controlling the heating unit depending on the determined temperature.

14. A method for applying radiation to a target region within a subject, wherein the method comprises:
   heating the target region by using a heating unit, determining a temperature along a length of an elongated introduction element, which has been inserted into the subject for introducing a radiation source emitting radiation to be applied to the target region into the subject, by a temperature determination unit, and controlling a moving unit for moving the radiation source within the introduction element such that the radiation source is located within, adjacent or surrounding the target region depending on the determined temperature by a control unit.

15. A non-transitory computer-readable storage medium in which computer-executable code is stored, the computer executable code configured to cause a computing device in which the non-transitory computer-readable storage medium is loaded to cause the system of claim 1 to perform the acts of:

inserting an elongated introduction element into a subject and introducing a radiation source emitting radiation to be applied to the target region into the subject, causing a moving unit to move a radiation source within the introduction element such that the radiation source is located within, adjacent or surrounding a target region, causing a heating unit to heat the target region, determining the temperature along the length of the introduction element using a temperature determination unit, and causing a control unit to move the moving unit depending on the determined temperature.

* * * * *